United States Patent [19]

Atwal

[11] Patent Number: 5,070,088
[45] Date of Patent: Dec. 3, 1991

[54] PYRANYL QUINOLINE CALCIUM CHANNEL BLOCKERS

[75] Inventor: Karnail Atwal, Newtown, Pa.

[73] Assignee: E. R. Squibb & Sons, Inc., Princeton, N.J.

[21] Appl. No.: 452,999

[22] Filed: Dec. 19, 1989

[51] Int. Cl.⁵ ............... C07D 491/052; A61K 31/44; A61K 31/47
[52] U.S. Cl. .................. 514/212; 514/291; 540/524; 546/89; 546/15; 544/238; 544/361
[58] Field of Search .......... 546/89; 540/524; 514/291, 212

[56] References Cited

U.S. PATENT DOCUMENTS 4,086,349 4/1978 Morinaka et al. ............... 514/291

OTHER PUBLICATIONS

V. A. Ashwood et al., "Synthesis and Antihypertensive Activity of 4-(Cyclic Amido)—2H—1-Benzopyrans", J. Med. Chem., 1986, 29, pp. 2194–2201.

Primary Examiner—Alan L. Rotman
Attorney, Agent, or Firm—Theodore R. Furman, Jr.; Suzanne E. Babajko

[57] ABSTRACT

Novel calcium channel blockers having the formula

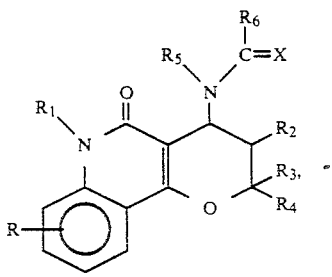

wherein X is oxygen or sulfur and wherein R, $R_1$, $R_2$, $R_3$, $R_4$, $R_5$, $R_6$ are as defined herein, are disclosed. These compounds are useful, for example, as anti-ischemic agents.

20 Claims, No Drawings

PYRANYL QUINOLINE CALCIUM CHANNEL BLOCKERS

SUMMARY OF THE INVENTION

In accordance with the present invention novel compounds having calcium channel blocking activity are disclosed. The compounds, which have utility, for example, as cardiovascular agents, have the general formula

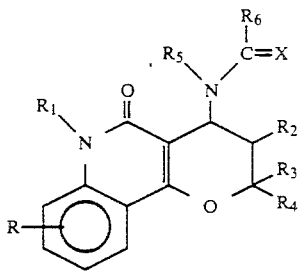

including pharmaceutically acceptable salts thereof, wherein

X is oxygen or sulfur;

R is hydrogen, alkyl, alkenyl, alkynyl, aryl, arylalkyl, haloalkyl, cycloalkyl, (cycloalkyl)alkyl, $-NO_2$, $-CN$, $-CF_3$, alkoxy or halo;

$R_1$ is hydrogen, alkyl, alkenyl, alkynyl, aryl, arylalkyl, haloalkyl, cycloalkyl, (cycloalkyl)alkyl;

$R_2$ is hydrogen, hydroxy, $-OCOR_1$, where $R_1 \neq$ hydrogen;

$R_3$ and $R_4$ are independently selected from hydrogen, alkyl, arylalkyl or taken together with the carbon atom to which they are attached form a 5-, 6- or 7-membered ring;

$R_5$ is $R_1$;

$R_6$ is $R_1$, heteroaryl, amino, substituted amino or $-OR_1$, where $R_1 \neq$ hydrogen, or $R_5$ and $R_6$ taken together with the nitrogen atom to which they are attached for a 5-, 6- or 7-membered saturated or unsaturated ring which may contain an additional nitrogen atom or an oxygen or sulfur atom.

DETAILED DESCRIPTION OF THE INVENTION

Listed below are definitions of various terms used to describe the compounds of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "alkenyl" and "alkynyl" refer to both straight and branched chain groups. Those groups having 2 to 10 carbon atoms are preferred.

The term "aryl" refers to phenyl and substituted phenyl. Exemplary substituted phenyl groups are phenyl groups substituted with 1, 2 or 3 groups independently selected from amino, alkylamino, dialkylamino, nitro, halogen, hydroxyl, trifluoromethyl, difluoromethoxy, alkyl of 1 to 4 carbon atoms, alkoxy of 1 to 4 carbon atoms, alkylthio of 1 to 4 carbon atoms, alkanoyloxy, cyano, carbonyl, or carboxyl groups.

The term "alkanoyl" refers to groups having the formula alkyl

Those alkanoyl groups having 2 to 11 carbon atoms are preferred.

The term "heteroaryl" refers to an aromatic heterocyclic group having at least one heteroatom in the ring. Preferred groups are pyridinyl, pyrrolyl, imidazolyl, furyl, thienyl, oxazolyl or thiazolyl.

The term "cycloalkyl" refers to groups having 3, 4, 5, 6 or 7 carbon atoms.

The term "halogen" refers to fluorine, chlorine, bromine and iodine.

The term "substituted amino" refers to a group of the formula $-NZ_1Z_2$ wherein $Z_1$ is hydrogen, alkyl, or aryl-$(CH_2)_m-$ and $Z_2$ is alkyl or aryl-$(CH_2)_m-$ (where m is 0 to 2) or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, or 1-pyrrolidinyl, 1-piperidinyl, or 1-azepinyl substituted with alkyl, alkoxy, alkylthio, halo, trifluoromethyl or hydroxy.

The compounds of formula I form acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Any other slat may then be formed from the free base and the appropriate inorganic or organic acid. Illustrative are the hydrohalides, especially the hydrochloride and hydrobromide, sulfate, nitrate, phosphate, borate, acetate, tartrate, maleate, citrate, succinate, benzoate, ascorbate, salicylate, methanesulfonate, benzenesulfonate, toluenesulfonate and the like.

The compounds of formula I, and the pharmaceutically acceptable salts thereof, are cardiovascular agents. They act as calcium entry blocking vasodilators and are useful as antihypertensive agents. Thus, by the administration of a composition containing one (or a combination) of the compounds of this invention, the blood pressure of a hypertensive mammalian (e.g., human) host is reduced. A single dose, or two to four divided daily doses, provided on a basis of about 0.1 to 100 milligrams per kilogram of body weight per day, preferably from about 1 to about 50 milligrams per kilogram per day, is appropriate to reduce blood pressure. The substance is preferably administered orally, but parenteral routes such as the subcutaneous, intramuscular or intravenous routes can also be employed.

As a result of the calcium entry blocking activity of the compounds of formula I, and the pharmaceutically acceptable salts thereof, these compounds, in addition to being antihypertensive agents, are especially useful as anti-ischemic agents, and are also useful as anti-arrhythmic agents, anti-anginal agents, anti-fibrillatory agents, anti-asthmatic agents, as an agent to increase the ratio of HDL-cholesterol to total serum cholesterol in the blood and in limiting myocardial infarction.

Additionally, the compounds of this invention are useful as therapy for congestive heart failure, therapy for peripheral vascular disease (e.g., Raynaud's disease), as anti-thrombotic agents, as anti-atherosclerotic agents, for treatment of cardiac hypertrophy (e.g., hypertrophic cardiomyopathy), for treatment of pulmonary hypertension, as an additive to cardioplegic solutions for cardiopulmonary bypasses and as an adjunct to thrombolytic therapy.

Compounds of this invention are also expected to be useful in the treatment of central nervous system vascular disorders, for example, as anti-stroke agents, anti-migraine agents, therapy for cerebral ischemia and therapy for subarachnoid hemorrhage, as well as in the treatment of central nervous system behavioral disorders, for example, in the treatment of psychiatric conditions including depression, mania, anxiety and schizophrenia, or for epilepsy or cognition benefit.

Further, compounds of this invention are expected to be used as anti-diarrheal agents, as therapy for dysmenorrhea, as therapy for tinnitus and other auditory and vestibulatory disorders, for the alleviation of the various forms of oedema, for reversal of adriamycin resistance, regulation of cell growth, for treatment of glaucoma, renal failure, hepatoxicity (e.g., liver cirrhosis), various endocrine hypersecretory states (e.g., diabetes, pheochromocytoma), drug-induced tardive dyskenesia, allergies, muscular dystrophy and cancer.

The compounds of this invention can also be formulated in combination with a beta-adrenergic agent, or antiarrhythmic agent, a diuretic such as chlorothiazide, hydrochlorothiazide, flumethiazide, hydroflumethiazide, bendroflumethiazide, methylchlothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories). Such combination products if formulated as a fixed dose employ the compounds of this invention within the does range described above and the other pharmaceutically active agent within its approved dose range.

The compounds of formula I can be formulated for use in the reduction of blood pressure in compositions such as tablets, capsules or elixirs for oral administration, or in sterile solutions or suspensions for parenteral administration. The compounds of formula I may also be administered via transdermal patch or nasal inhalation solutions. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

To prepare the compounds of formula I, a compound of the formula

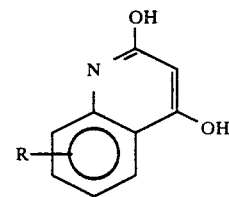

is reacted with an aldehyde of the formula

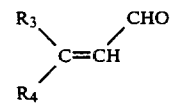

in an organic solvent, e.g. pyridine, and in the presence of a dehydrating agent, e.g. anhydrous magnesium sulfate, to provide a compound having the formula

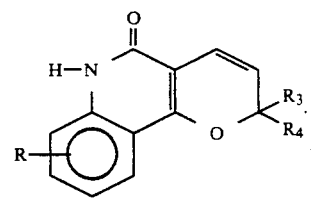

Compound IV can be reacted with a compound of the formula

wherein L is a leaving group such as halogen or 0-tosylate, in a solvent, e.g. dimethylformamide, and in the presence of a base, e.g. potassium carbonate, to provide a compound having the formula

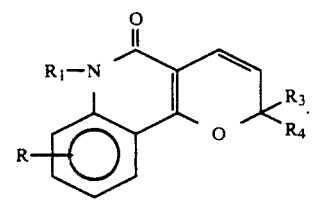

Compound VI in solvents, e.g. water and dimethylsulfoxide, is thereafter treated with an N-bromosuccinimide, to provide a compound of the formula

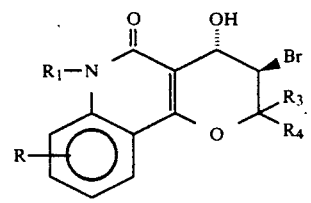

Compound VII in a solvent, such as tetrahydrofuran, can be treated with a compound of the formula

in a solvent, e.g. ethanol, to provide

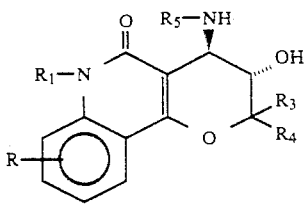

which can thereafter be reacted in a solvent, e.g. tetrahydrofuran, in the presence of a base, e.g. sodium carbonate, with a compound of the formula

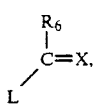

wherein L is a leaving group, to provide a compound of formula I wherein $R_5$ and $R_6$ are other than a cyclic group.

Compounds of formula I wherein $R_5$ and $R_6$ form a cyclic group can be prepared by first reacting a compound of formula IX with a compound of formula X containing another leaving group L' in the $R_6$ moiety, i.e.

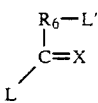

to yield compounds of formula

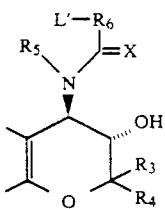

which can be cyclized in the presence of a base.

Preferred compounds of the present invention are those wherein

R is hydrogen;

$R_1$ is arylalkyl;

$R_2$ is —OH;

$R_3$ and $R_4$ are each alkyl;

$R_5$ and $R_6$ and the nitrogen and carbon atoms to which they are attached form a cyclic group; and X is oxygen.

Most preferred are those compounds wherein

R is hydrogen;

$R_1$ is benzyl;

$R_2$ is trans-OH;

$R_3$ and $R_4$ are each methyl;

$R_5$, $R_6$, the nitrogen and carbon atoms to which they are attached, and X form the group

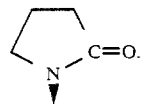

The invention will be further described by the following Examples.

EXAMPLE 1 (SQ 33,757)

trans-4-(4-Chloro-1-oxobutyl)amino]-2,3,4,6-tetrahydro-3-hydroxy-2,2-dimethyl-6-(phenylmethyl)-5H-pyrano[3,2-c]quinolin-5-one A. 2,6-Dihydro-2,2-dimethyl-5H-pyrano[3,2-c]-quinolin-5-one To a boiling solution of 2,4-dihydroxy quinoline (5.0 g, 31 mmol) in pyridine (300 ml) under argon was added anhydrous magnesium sulfate (20 g) followed by 3-methyl-2-butenal (2.6 g, 31.0 mmole). The reaction was heated under reflux for 16 hours. After 12 hours, more 3-methyl-2-butenal (1.3 g, 15.5 mmol) was added and the reaction was heated under reflux for 16 more hours. The reaction was diluted with 10% methanol in chloroform (200 ml) and filtered while hot. The solid was washed with hot solvent (10% methanol in chloroform) and the filtrate was concentrated in vacuo and co-evaporated with toluene. The resulting solid was triturated with isopropyl ether to give the title A compound (4.5 g), m.p. 174° C.-177° C.: $^1$H NMR (DMSO-$d_6$/CDCl$_3$) ppm: δ7.7 (d, 1H, J =8.0 Hz), 7.4 (d, 1H, J =9.0 Hz), 7.2 (d, 1H, J =8.0 Hz), 7.1 (dd, 1H, J =7 & 8 Hz), 6.5 (d, 1H, J =8.0 Hz), 5.5 (d, 1H, J =9.0 Hz), 3.3 (s, 1H), 1.34 (2 s, 6H); $^{13}$C NMR (DMSO-$d_6$/CDCl$_3$) ppm: 160.8, 158.7, 136.5, 128.9, 120.9, 120.2, 119.7, 115.0, 113.6, 113.4, 103.7, 76.7, 26.0.

B. 2,6-Dihydro-2,2-dimethyl-6-(phenylmethyl)-5H-pyrano[3,2-c]quinolin-5-one

To a solution of the title A compound (1.0 g, 4.4 mmole) in dimethylformamide (10 ml) under argon was added powdered anhydrous potassium carbonate (0.9 g, 6.6 mmol) followed by benzyl bromide (0.83 g, 4.8 mmole) and 18-crown-6 (20 mg). The reaction mixture was stirred at room temperature for 16 hours. It was then poured into water (50 ml) and extracted with ethyl acetate (3 ×150 ml). The organic layer was washed with water, dried over anhydrous magnesium sulfate and evaporated in vacuo. The residue was purified by flash chromatography (7:3, Hexane/ethyl acetate) to give the title B compound as a colorless solid (0.5 g), m.p. 91° C.-92° C.: $^1$H NMR (CDCl$_3$) ppm: δ7.8 (d, 1H, J =8.0 Hz), 7.0 (m, 8H), 6.65 (d, 1H, J =10.0 Hz), 5.3 (d, 1H, J =10.0 Hz), 5.2 (s, 2 H), 1.3 (s, 6 H); $^{13}$C NMR (CDCl$_3$) ppm: 160.7, 155.2, 138.4, 136.5, 130.5, 128.3, 127.8, 126.6, 126.4, 126.2. 126.0, 122.8, 121.5, 117.6, 115.8, 114.5, 105.1, 78.6, 45.3, 28.0.

C. trans-3-Bromo-2,3,4,6-tetrahydro-4-hydroxy-2,2-dimethyl-6-(phenylmethyl)-5H-pyrano-[3,2-c]quinolin-5-one To a solution of the title B compound (6.0 g, 18.9 mmole) in dimethylsulfoxide/water (20:5) was added N-bromosuccinimide (3.4 g, 18.9 mmole) in one portion at 0° C. The reaction mixture was stirred for ~30 minutes. It was then poured into water (50 ml) and extracted with ethyl acetate. The organic layer was washed with water, dried over anhydrous magnesium sulfate and concentrated in vacuo to give a colorless residue which was triturated with isopropyl ether to give the title C compound (6.0 g) m p 120° C.–123° C., ¹H NMR (CDCl₃) ppm: δ7.8 (d, 1H, J = 8.0 Hz), 7.1 (m, 8H), 5.53 (s, 2 H), 4.9 (d, 1 H, J = 7.0 Hz), 4.1 (d, 1 H, J = 7.0 Hz), 1.6 (s, 3 H), 1.4 (s, 3 H); ¹³C NMR (CDCl₃) ppm: 162.8, 154.9, 138.2, 135.9, 131.2, 130.5, 128.4, 128.3, 127.9, 126.7, 126.4, 126.1, 123.4 122.0, 115.4, 114.7, 105.9, 80.8, 67.7. 26.9, 21.8.

D.  trans-4-Amino-2,3,4,6-tetrahydro-3-hydroxy-2,2-dimethyl-6-(phenylmethyl)-5H-pyrano-[3,2-c]quinolin-5-one To a suspension of the title C compound (6.0 g, 14.5 mmole) in tetrahydrofuran (40 ml) was added absolute ethanol (10 ml) and concentrated ammonium hydroxide solution (15 ml). The reaction mixture was stirred at room temperature for 16 hours. It was then concentrated in vacuo and coevaporated with toluene (2×50 ml) to give crude title D compound (5.0 g) as an oil. The crude material was used in the next step without purification.

E.  trans-4-[(4-Chloro-1-oxobutyl)amino]-2,3,4,6-tetrahydro-3-hydroxy-2,2-dimethyl-6-(phenylmethyl)-5H-pyrano[3,2-c]quinolin-5-one To a solution of the crude title D compound from above (5.0 g, 14.0 mmole) in 20 percent aqueous tetrahydrofuran (40 ml) was added 4-chlorobutyryl chloride (3.1 g, 21.5 mmole) dropwise. The pH of the reaction was maintained between 8.5–9.0 by simultaneous addition of 25 percent aqueous solution of sodium carbonate. After completion of addition, the reaction mixture was stirred for one more hour. The solvent was evaporated in vacuo and the residue was diluted with ethyl acetate. Organic layer was washed with water, dried over anhydrous magnesium sulfate and concentrated in vacuo to give the crude product as an oil. It was purified by flash chromatography on silica gel (20%–80% ethyl acetate in hexanes) to give the title compound (2.0 g) as an off white solid, m.p. 176° C.–178° C.: ¹H NMR (CDCl₃) ppm: δ6 8.0 (d, 1 H, J = 8.0 Hz), 7.5 (d, 1 H, J = 7.0 Hz), 7.3 (m, 7 H), 5.5( s, 2 H), 4.7 (dd, J = 8.0 & 2.0 Hz, 1H), 3.9 (d, J = 8.0 Hz, 1 H), 3.6 (m, 2 H), 2.5 (m, 2 H), 2.1 (m, 2 H), 1.6 (s, 3 H), 1.3 (s, 3 H); ¹³C NMR (CDCl₃) ppm: 175.0, 162.7, 138.7, 136.3, 131.7, 128.9, 127.4, 126.5, 124.2, 122.4, 114.9, 102.9, 81.0, 74.8, 52.9, 45.7, 44.3, 33.8, 28.3, 26.4, 18.5.

EXAMPLE 2 (SQ 33,757)

trans-2,3,4,6-Tetrahydro-3-hydroxy-2,2-dimethyl-4-(2-oxo-1-pyrrolidinyl)-6-(phenylmethyl)-5H-pyrano[3,2-c]quinolin-5-one To a solution of the title compound of Example 1 (2.0 g, 4.4 mmole) in dry tetrahydrofuran/dimethylsulfoxide (20: 1 ml) was added sodium hydride (50% oil dispersion, 0.3 g, 6.6 mmol). The reaction mixture was stirred at room temperature under argon for 16 hours. The reaction was quenched with water (2 ml) and the solvent was evaporated in vacuo. The residue was diluted with ethyl acetate and washed with water and brine. After drying over anhydrous magnesium sulfate, the solvent was evaporated to give 1.8 g of the product. This solid was triturated with dichloromethane to give the title compound (1.2 g) as a white solid, m.p. >260° C.; IR (KBr): 1090.9, 1131.2, 1394.9, 1628.7, 1683.2, 3358.2, 3364.2, 3372.3, 3374.8 cm⁻¹: ¹H NMR (CDCl₃) ppm: δ7.85 (d, J = 8.0 Hz, 1 H), 7.5 (d, J = 8.0 Hz, 1H), 7.2 (m, 7 H), 5.7 (s, 1 H), 5.4 (dd, J = 15.0, 14.0 Hz, 2 H), 3.86 (s, 1 H), 3.59 (s, 1 H), 3.25 (m, 1 H), 3.05 (m, 1 H), 2.5 (m, 2 H), 2.0 (m, 2 H), 1.48 (s, 3 H), 1.27 (s, 3 H); ¹³C NMR (DMSO/CDCl₃) ppm: 170.3, 147.2. 141.1, 138.5, 136.9, 136.4, 133.0, 131.6, 125.2, 124.9, 90.8. 54.2, 50.5, 50.3, 36.2. 35.5, 28.2, 28.0.

Analysis calc'd for $C_{25}H_{26}N_2O_4 \cdot 0.69 H_2O$:
C, 69.67: H, 6.40; N, 6.49;
Found: C, 69.67; H, 6.25; N, 6.37.

EXAMPLE 3 (SQ 34,087)

trans-4-[(4-Chloro-1-oxobutyl)amino]-2,3,4,6-tetrahydro-3-hydroxy-6-[(4-methoxyphenyl)methyl]-2,2-dimethyl-5H-pyrano(3,2-c)quinolin-5-one A.  2,6-Dihydro-6-[(4-methoxyphenyl)methyl]-2,2-dimethyl-5H-pyrano(3,2-c)quinolin-5-one To a solution of the title A compound of Example 1 (8.0 g, 35 mmole) in dimethylformamide (50 ml) under argon was added powdered anhydrous potassium carbonate (34.3 g, 248 mmol) followed by 4-methoxybenzyl chloride (11.2 g, 74 mmole). The reaction mixture was stirred at room temperature for 16 hours. It was then poured into water (50 ml) and extracted with ethyl acetate (3×150 ml). The organic layer was washed with water, dried over anhydrous magnesium sulfate and evaporated in vacuo. The residue was flash chromatographed (10% ethyl acetate in hexanes) to give the title A compound (3.0 g) as an oil: ¹H NMR (CDCl₃) ppm: δ7.95 (d, 1H, J = 8.0 Hz), 7.4 (m, 1H), 7.2 (d, 1 H, J = 8.0 Hz), 7.15 (d, 2 H, J = 10.0 Hz), 6.8 (d, 1H, J = 10.0 Hz), 5.55 (d, 1H, J = 10.0 Hz), 5.45 (s, 2 H), 3.7 (s, 3 H), 1.5 (s, 6 H); ¹³C NMR (CDCl₁) ppm: 161.1, 158.7, 155.4, 138.8. 130.9. 130.8, 128.9. 127.9, 126.3. 123.1, 121.7, 117.9. 116.3. 114.1. 113.4, 105.6, 78.9, 55.2, 55.0, 45.2, 28.3.

B.  trans-3-Bromo-2,3,4,6-tetrahydro-4-hydroxy-6-[(4-methoxyphenyl)methyl]-2,2-dimethyl-5H-pyrano(3,2-c)quinolin-5-one To a solution of the title A compound (2.5 g, 7.2 mmole) in dimethylsulfoxide/water (16:4) was added N-bromosuccinimide (1.4 g, 7.9 mmole) in one portion at 0° C. The reaction mixture was stirred for ~30 minutes at room temperature. It was then poured into water (50 ml) and extracted with ethyl acetate. The organic layer was washed with water, dried over anhydrous magnesium sulfate and concentrated in vacuo to give a colorless residue. It was crystallized from dichloromethane-isopropyl ether to give the title B compound (1.5 g), m.p. 146° C.–147° C.; ¹H NMR (CDCl₃) ppm: δ7.9 (d, 1H, J = 8.0 Hz), 7.3 (m, 5H), 6.8 (d, 2 H, J = 9.0 Hz), 5.5 (m, 2 H), 5.1 (d, 1 H, J = 8.0 Hz), 4.2 (d, 1 H, J = 8.0 Hz), 3.7 (s, 3 H), 1.7 (s, 3 H), 1.5 (s, 3 H); ¹³C NMR (CDCl₃) ppm: 162.8, 154.9, 138.2, 135.9, 131.2, 130.5, 128.4, 128.3, 127.9, 126.7, 126.4. 126.1, 123.4. 122.0, 115.4, 114.7, 105.9, 80.8, 67.7, 26.9, 21.8.

C.  trans-4-Amino-2,3,4,6-tetrahydro-3-hydroxy-6-[(4-methoxyphenyl)methyl]-2,2-dimethyl-5H-pyrano(3,2-c)quinolin-5-one To a suspension of the title B compound (1.5 g, 3.4 mmole) in tetrahydrofuran (30 ml) was added absolute ethanol (10 ml) and concentrated ammonium hydroxide solution (30 ml). The reaction mixture was stirred at room temperature for 4 days. It was then concentrated in vacuo and coevaporated with toluene (2×50 ml) to give the title C compound as an oil. The crude material was used in the next step without purification.

D.  trans-4-[(4-Chloro-1-oxobutyl)amino]-2,3,4,6-tetrahydro-3-hydroxy-6-[(4-methoxyphenyl)methyl]-2,2-dimethyl-5H-pyrano-(3,2-c)quinolin-5-one To a solution of the title C compound (1.2 g, 3.2 mmole) in 20 percent aqueous tetrahydrofuran (40 ml) was added 4-chlorobutyryl chloride (0.7 g, 5.1 mmole) dropwise. The pH of the reaction was maintained between 8.5-9.0 by simultaneous addition of 25 percent aqueous solution of sodium carbonate. After completion of addition, the reaction mixture was stirred for one more hour. The solvent was evaporated in vacuo and the residue was diluted with ethyl acetate. The organic layer was washed with water, dried over anhydrous magnesium sulfate and concentrated in vacuo to give the crude product as an oil. It was triturated with dichloromethane-isopropyl ether to give the title compound (0.9 g) as an off white solid, m.p. 218° C.–219° C.: $^1$H NMR (CDCl$_3$/DMSO) ppm: δ7.9 (d, 2 H, J =8.0 Hz), 7.4 (m, 1 H), 7.3 (m, 1 H), 7.1 (d, 3 H, J =4.0 Hz), 6.8 (m, 2 H), 5.4 (m, 3 H), 4.7 (s, 1 H), 3.6 (m, 3 H), 3.3 (s, 3 H), 2.2 (m, 2 H), 2.0 (m, 2 H), 1.4 (s, 6 H).

EXAMPLE 4 (SQ 34,087)

trans-2,3,4,6-Tetrahydro-3-hydroxy-6-[(4-methoxyphenyl)methyl-2,2-dimethyl-4-(2-oxo-1-pyrrolidinyl)-5H-pyrano(3,2-c)quinolin-5-one To a solution of the title compound of Example 3 (0.9 g, 3.2 mmol) in dry dimethylsulfoxide (5 ml) was added sodium hydride (50% oil dispersion, 0.15 g, 3.2 mmol). The reaction mixture was stirred at room temperature under argon for 16 hours. The reaction was quenched with water (2 ml), solvent was evaporated in vacuo, and the residue was diluted with ethyl acetate. Organic layer was washed with water, brine, dried over anhydrous magnesium sulfate and concentrated in vacuo to give a colorless product (1.8 g). This solid was triturated with dichloromethane to give the title compound (0.5 g) as a white solid, m.p. 243° C.–245° C.: $^1$H NMR (DMSO) ppm: δ7.85 (d, J =7.0 Hz, 1 H), 7.5 (t, J =7.0 Hz, 1H), 7.3 (d, 1 H, J =8.0 Hz), 7.2 (t, 1 H, J =8.0 & 7.0 Hz), 7.1 (d, 2 H, J =9.0 Hz), 6.8 (d, 2 H, J =9.0 Hz), 5.7 (s, 1 H), 5.4 (m, 2 H), 3.7 (s, 3H), 3.2 (m, 2 H), 2.2 (m, 2 H), 1.9 (m, 2 H), 1.5 (s, 3H), 1.27 (s, 3H).

EXAMPLE 5 (SQ 34,087)

trans-2,3,4,6-Tetrahydro-3-hydroxy-2,2-dimethyl-4-(2-oxo-1-pyrrolidinyl)-5H-pyrano(3,2-c)quinolin-5-one A solution of the title compound of Example 1 (0.48 g, 1.1 mmol) in trifluoroacetic acid (1.5 mL) was heated under reflux for 3 hours. It was then concentrated in vacuo and triturated with isopropanol to give 0.15 g of the product. The mother liquor was purified by preporative thin layer chromatography, eluting with 10 percent methanol in chloroform. The combined solid was crystallized from acetonitrile to yield the title compound, m.p. 256° C.–258° C.: $^1$H NMR (DMSO) δ11.2 (s, 1H), 7.7 (d, J =8.0 Hz, 1 H), 7.48 (m, 1 H), 7.25 (d, J =9.0 Hz, 1 H), 7.1 (t, J =7.0 Hz, 1 H), 5.6 (br, 1 H), 4.5 (br, 1 H), 3.8 (s, 1 H), 3.2 (m, 2 H), 2.2 (m, 2 H), 1.9 (m, 2 H), 1.5 (s, 3 H), 1.2 (s, 3 H); IR (KBr) 1081.3, 1130.8, 1390.5, 1605.2, 1646.2, 3422.8 cm$^{-1}$.

Analysis calc'd for C$_{18}$H$_{20}$N$_2$O$_4$:
C, 65.B4; H, 6.16; N, 8.53;
Found: C, 65.63; H, 6.11; N, 8.47.

EXAMPLES 6–20

Utilizing the procedures outlined above and in Examples 1–6, the following compounds within the scope of the present invention can be prepared.

EXAMPLE 6

(trans)-2,3,4,6-Tetrahydro-3-hydroxy-2,2,6-trimethyl-4-(2-oxo-1-pyrrolidinyl)-5H-pyrano-[3,2-c]quinolin-5-one

EXAMPLE 7

(trans)-2,3,4,6-Tetrahydro-3-hydroxy-2,2-dimethyl-4-(2-oxo-1-pyrrolidinyl)-6-propyl-5H-pyrano[2,3-c]-quinolin-5-one

EXAMPLE 8

(trans)-2,3 4,6-Tetrahydro-3-hydroxy2,2-dimethyl-4-(2-oxo-1-pyrrolidinyl)-6-(cyclohexylmethyl)-5H-pyrano[3,2-c]quinolin-5-one

EXAMPLE 9

(trans)-2,3,4,6-Tetrahydro-3-hydroxy-2,2-dimethyl-4-(2-oxo-1-pyrrolidinyl)-6-(2-propenyl)-5H-pyrano-[3,2-c]quinolin-5-one

EXAMPLE 10

(trans)-2,3,4-6-Tetrahydro-3-hydroxy-2,2-dimethyl-4-(2-oxo-1-pyrrolidinyl)-6-(2,2,2-trifluoroethyl)-5H-pyrano[3,2-c]quinolin-5-one

EXAMPLE 11

(trans)-2,3,4,6-Tetrahydro-3-hydroxy-2,2-dimethyl-4-acetamido-6-[(3-methylphenyl)methyl]-5H-pyrano-[3,2-c]quinolin-5-one

EXAMPLE 12

(trans)-2,3,4,6-Tetrahydro-3-hydroxy-2,2-dimethyl-4-(3,3-dimethylureido)carbonylamino]-6-[(4-nitrophenyl)methyl]-5H-pyrano[3,2-c]quinolin-5-one

EXAMPLE 13

(trans)-2,3,4,6-Tetrahydro-3-hydroxy-2,2-dimethyl-4-[(ethoxycarbonyl)amino]-6-[(4-chlorophenyl)methyl]-5H-pyrano[3,2-c]quinolin-5-one

EXAMPLE 14

(trans)-2,3,4,6-Tetrahydro-3-hydroxy-2,2-dimethyl-4-(acetylethylamino)-6-[[4-(trifluoromethyl)-phenyl]methyl]-5H-pyrano3,2-c]quinolin-5-one

EXAMPLE 15

(trans)-2,3,4,6-Tetrahydro-3-hydroxy-2,2-dimethyl-4-(2-oxo-1-piperidinyl)-6-(phenylmethyl)-5H-pyrano-[3,2-c]quinolin-5-one

EXAMPLE 16

(trans)-2,3,4-6-Tetrahydro-3-hydroxy-2,2-dimethyl-4-[tetrahydro-6-oxo-1)2H)-pyridazinyl)-6-(phenylmethyl)-5H-pyrano[3,2-c]quinolin-5-one

EXAMPLE 17

(trans)-2,3,4,6-Tetrahydro-3-hydroxy-2,2-spriocyclopentyl-4-(2-thioxo-1pyrrolidinyl)-6-(phenylmethyl)-5H-pyrano-[3,2-c]quinolin-5-one

EXAMPLE 18

(trans)-2,3,4,6-Tetrahydro-3-acetyloxy)-2,2-dimethyl-4-(2-oxo-1-pyrrolidinyl)-6-(phenylmethyl)-5H-pyrano[3,2-c]quinolin-5-one

EXAMPLE 19

(trans)-2,3,4,6-Tetrahydro-3-hydroxy-2,2-dimethyl-4-(3-methyl-2-oxo-1-imidazolidinyl)-6-(phenylmethyl)-5H-pyrano[3,2-c]quinolin-5-one

EXAMPLE 20

(trans)-2,3,4,6-Tetrahydro-3-hydroxy-2,2-spirocyclopentyl-4-(4-methyl-2-oxo-1-piperazinyl)-6-(phenylmethyl)-5H-pyrano3,2-c]quinolin-5-one

What is claimed is:

1. A compound having the formula

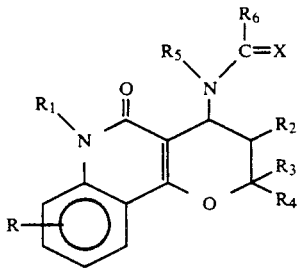

or a pharmaceutically acceptable salt thereof, wherein
X is oxygen or sulfur;
R is hydrogen, alkyl, alkenyl, alkynyl, aryl, arylalkyl, haloalkyl, cycloalkyl, (cycloalkyl)alkyl, $-NO_2$, $-CN$, $-CF_3$, alkoxy or halo;
$R_1$ is hydrogen, alkyl, alkenyl, alkynyl, aryl, arylalkyl, haloalkyl, cycloalkyl, (cycloalkyl)alkyl;
$R_2$ is hydrogen, hydroxy, $-OCOR_1$, where $R_1 \neq$ is not hydrogen;
$R_3$ and $R_4$ are independently hydrogen, alkyl, or arylalkyl;
$R_5$ is $R_1$;
$R_6$ is $R_1$, amino, substituted amino or $-OR_1$, where $R_1$ is not hydrogen, or $R_5$ and $R_6$ taken together with the nitrogen and carbon atoms to which they are attached form a 5-, 6- or 7-membered saturated ring;
wherein the terms "alkyl" and "alkoxy" refers to both straight and branched chain groups having 1 to 10 carbon atoms;
the terms "alkenyl" and "alkynyl" refer to both straight and branched cain groups having 2 to 10 carbon atoms;
the term "aryl" refers to phenyl and monosubstituted phenyl wherein the substitutent may be amino, alkylamino, dialkylamino, nitro, halogen, hydroxyl, trifluoromethyl, difluoromethoxy, alkyl of 1 to 4 carbon atoms, alkoxy of 1 to 4 carbon atoms, alkylthio of 1 to 4 carbon atoms, alkanoyloxy, cyano, carbonyl, or carboxyl groups;
the term "alkanoyloxy" refers to groups having the formula alkyl

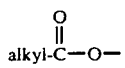

and containing 2 to 11 carbon atoms;
the term "cycloalkyl" refers to groups having 3, 4, 5, 6 or 7 carbon atoms;
the term "halogen" refers to fluorine, chlorine, bromine and iodine;
the term "substituted amino" refers to a group of the formula $-NZ_1Z_2$ wherein $Z_1$ is hydrogen, alkyl, or aryl-$(CH_2)_m-$ and $Z_2$ is alkyl or aryl-$(CH_2)_m-$ (where m is 0 to 2); and
the term "arylalkyl" refers to groups containing aryl and alkyl moieties as defined above.

2. A compound of claim 1 wherein
R is hydrogen;
$R_1$ is arylalkyl;
$R_2$ is $-OH$;
$R_3$ and $R_4$ are each alkyl;
$R_5$ and $R_6$ and the nitrogen and carbon atoms to which they are attached form a 5-, 6- or 7-membered saturated heterocyclic ring; and
X is oxygen.

3. A compound of claim 1 wherein
R is hydrogen;
$R_1$ is benzyl;
$R_2$ is trans-OH;
$R_3$ and $R_4$ are each methyl;
$R_5$, $R_6$, the nitrogen and carbon atoms to which they are attached, and X form the group

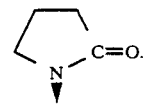

4. A compound of claim 1 having the name trans-4-[(4-chloro-1-oxobutyl)amino]-2,3,4,6-tetra-hydro-3-hydroxy-2,2-dimethyl-6-(phenylmethyl)-5H-pyrano[3,2-c]quinolin-5-one.

5. A compound of claim 1 having the name trans-2,3,4,6-tetrahydro-3-hydroxy-2,2-dimethyl-4-(2-oxo-1-pyrrolidinyl)-6-(phenylmethyl)-5H-pyrano[3,2-c]quinolin-5-one.

6. A compound of claim 1 having the name trans-4-[(4-chloro-1-oxobutyl)amino]-2,3,4,6-tetrahydro-3-hydroxy-6-[(4-methoxyphenyl)methyl]-2,2-dimethyl-5H-pyrano(3,2-c)quinolin-5-one.

7. A compound of claim 1 having the name trans-2,3,4,6-tetrahydro-3-hydroxy-6-[(4-methoxyphenyl)methyl]-2,2-dimethyl-4-(2-oxo-1-pyrrolidinyl)-5H-pyrano(3,2-c)quinolin-5-one.

8. A compound of claim 1 having the name trans-2,3,4,6-tetrahydro-3-hydroxy-2,2-dimethyl-4-(2-oxo-1-pyrrolidinyl)-5H-pyrano(3,2-c)quinolin-5-one.

9. A compound of claim 1 having the name (trans)-2,3,4,6-tetrahydro-3-hydroxy-2,2,6-trimethyl-4-(2-oxo-1-pyrrolidinyl)-5H-pyrano[3,2-c]quinolin- 5-one.

10. A compound of claim 1 having the name (trans)-2,3,4,6-tetrahydro-3-hydroxy-2,2-dimethyl-4-(2-oxo-1-pyrrolidinyl)-6-propyl-5H-pyrano[2,3-c]-quinolin-5-one.

11. A compound of claim 1 having the name (trans)-2,3,4,6-tetrahydro-3-hydroxy-2,2-dimethyl-4-(2-oxo-1-pyrrolidinyl)-6-(cyclohexylmethyl)-5H-pyrano[3,2-c]quinolin-5-one.

12. A compound of claim 1 having the name (trans)-2,3,4,6-tetrahydro-3-hydroxy-2,2-dimethyl-4-(2-oxo-1-pyrrolidinyl)-6-(2-propenyl)-5H-pyrano-[3,2-c]quinolin-5-one.

13. A compound of claim 1 having the name (trans)-2,3,4-6-tetrahydro-3-hydroxy-2,2-dimethyl-4-(2-oxo-1-pyrrolidinyl)-6-(2,2,2-trifluoroethyl)-5H-pyrano[3,2-c]quinolin-5-one.

14. A compound of claim 1 having the name (trans)-2,3,4,6-tetrahydro-3-hydroxy-2,2-dimethyl-4-acetamido-6-[(3-methylphenyl)methyl]-5H-pyrano-[3,2-c]quinolin-5-one.

15. A compound of claim 1 having the name (trans)-2,3,4,6-tetrahydro-3-hydroxy-2,2-dimethyl-4-(3,3-dimethylureido)carbonyl]amino]-6-[(4-nitrophenyl)methyl]-5H-pyrano[3,2-c]quinolin-5-one.

16. A compound of claim 1 having the name (trans)-2,3,4,6-tetrahydro-3-hydroxy-2,2-dimethyl-4-[(ethoxycarbonyl)amino]-6-[(4-chlorophenyl)methyl]-5H-pyrano[3,2-c]quinolin-5-one.

17. A compound of claim 1 having the name (trans)-2,3,4,6-tetrahydro-3-hydroxy-2,2-dimethyl-4-(acetylethylamino)-6-[[4-(trifluoromethyl)-phenyl]methyl]-5H-pyrano[3,2-c]quinolin-5-one.

18. A compound of claim 1 having the name (trans)-2,3,4,6-tetrahydro-3-hydroxy-2,2-dimethyl-4-(2-oxo-1-piperidinyl)-6-(phenylmethyl)-5H-pyrano-[3,2-c]quinolin-5-one.

19. A compound of claim 1 having the name (trans)-2,3,4,6-tetrahydro-3-(acetyloxy)-2,2-dimethyl-4-(2-oxo-1-pyrrolidinyl)-6-(phenylmethyl)-5H-pyrano[3,2-c]quinolin-5-one.

20. A method for the treatment of ischemia in a mammalian host comprising administering to a mammalian host in need thereof, a therapeutically effective amount of a compound of claim 1.

* * * * *